(12) United States Patent
Lusis et al.

(10) Patent No.: US 8,431,717 B2
(45) Date of Patent: Apr. 30, 2013

(54) PROCESS FOR THE PREPARATION OF 5-(2-ETHYL-DIHYDRO-1H-INDEN-2-YL)-1H-IMIDAZOLE AND SALTS THEREOF

(75) Inventors: Viesturs Lusis, Riga (LV); Dzintra Muceniece, Riga (LV); Inese Reine, Riga (LV); Armands Zandersons, Riga (LV)

(73) Assignee: JSC Grindeks, Riga (LV)

( * ) Notice: Subject to any disclaimer, the term of this patent is extended or adjusted under 35 U.S.C. 154(b) by 451 days.

(21) Appl. No.: 12/734,777

(22) PCT Filed: Dec. 3, 2008

(86) PCT No.: PCT/EP2008/066709
§ 371 (c)(1),
(2), (4) Date: Sep. 20, 2010

(87) PCT Pub. No.: WO2009/071584
PCT Pub. Date: Jun. 11, 2009

(65) Prior Publication Data
US 2011/0028733 A1 Feb. 3, 2011

(30) Foreign Application Priority Data
Dec. 5, 2007 (EP) ................................. 07122400

(51) Int. Cl.
*C07D 233/64* (2006.01)
*C07D 233/54* (2006.01)
*C07D 233/58* (2006.01)

(52) U.S. Cl.
USPC ....................................... 548/344.1; 548/345.1

(58) Field of Classification Search ............... 548/344.1, 548/345.1
See application file for complete search history.

(56) References Cited

U.S. PATENT DOCUMENTS
3,767,668 A * 10/1973 Buchel et al. ............. 548/344.1
3,872,095 A * 3/1975 Buchel et al. ............. 548/344.1

FOREIGN PATENT DOCUMENTS
EP 247764 A1 * 12/1987
EP 310745 A2 * 4/1989

* cited by examiner

*Primary Examiner* — Jason M Nolan
(74) *Attorney, Agent, or Firm* — Hueschen and Sage

(57) ABSTRACT

The invention provides an improved, highly efficient method for preparing 5-(2-ethyl-2,3-dihydro-1H-inden-2-yl)-1H-imidazole, and its salts, in particular its pharmaceutically acceptable salts.

8 Claims, No Drawings

PROCESS FOR THE PREPARATION OF 5-(2-ETHYL-DIHYDRO-1H-INDEN-2-YL)-1H-IMIDAZOLE AND SALTS THEREOF

TECHNICAL FIELD

The present invention provides processes and intermediates useful in the preparation of 5-(2-ethyl-2,3-dihydro-1H-inden-2-yl)-1H-imidazole (international non-proprietary name—"Atipamezole") and salts, in particular pharmaceutically acceptable salts, thereof, a potent and selective $\alpha_2$-receptor antagonist.

BACKGROUND ART

EP 0310745 B (FARMOS OY) Apr. 12, 1989 disclosed preparation of 5-(2-ethyl-2,3-dihydro-1H-inden-2-yl)-1H-imidazole salt by two synthetic routes.

First synthetic route as starting material was used 2-acetyl-1-indanone, which was alkylated with ethylbromide in acetone in the presence of sodium carbonate to 2-acetyl-2-ethyl-1-indanone. The acetyl group was brominated with bromine in methanol and to imidazole by heating in formamide. Then the intermediate was hydrogenated in 2N hydrochloric acid in the presence of 10% palladium on carbon.

Second synthetic route disclosed in the same patent is following, as starting material was used 2,3-dihydro-1H-indene-2-carboxylic acid methyl ester, which was prepared by methylation of 2,3-dihydro-1H-indene-2-carboxylic acid in the presence of sulphuric acid. The 2,3-dihydro-1H-indene-2-carboxylic acid methyl ester was reacted with N-isopropylcyclohexylamide and ethylbromide yielding 2,3-dihydro-2-ethyl-1H-indene-2-carboxylic acid, then thionyl chloride was added and 2,3-dihydro-2-ethyl-1H-indene-2-carboxylic acid chloride was obtained. In the next step ethoxymagnesiummalonic acid ethyl ester in dry ether was added to 2,3-dihydro-2-ethyl-1H-indene-2-carboxylic acid chloride and reaction mixture was treated with sulphuric acid, and 1-(2,3-dihydro-2-ethyl-1H-inden-2-yl)ethanone was obtained, then the intermediate was stirred in methylene chloride and bromine was added by giving a new intermediate 2-bromo-1-(2,3-dihydro-2-methyl-1H-inden-2-yl)ethanone, to which was thereafter added formamide and hydrochloric acid yielding crude product of 5-(2-ethyl-2,3-dihydro-1H-inden-2-yl)-1H-imidazole. The last step involved hydrogenation of the crude product of 5-(2-ethyl-2,3-dihydro-1H-inden-2-yl)-1H-imidazole with 10% palladium on carbon.

EP 0247764 B (ORION-YHTYMÄ OY) Feb. 12, 1987 disclosed the following process for preparation of 5-(2-ethyl-2,3-dihydro-1H-inden-2-yl)-1H-imidazole hydrochloride. The process starts by reaction of alpha, alpha'-dibromo-o-xylene with 4-penten-2-one to obtain 1-(2,3-dihydro-2-vinyl-1H-inden-2-yl)ethanone. The obtained intermediate was brominated, e.g. with bromine, methylene chloride was used as solvent and 2-bromo-1-(2,3-dihydro-2-vinyl-1H-inden-2-yl)-ethanone was obtained, which is thereafter reacted with formamide in excess formamide to give a 4(5)-(2,3-dihydro-2-vinyl-1H-inden-2-ylimidazole hydrochloride. As the last step the vinyl group was catalytically hydrogenated to an ethyl group so as to form a product 4(5)-(2,3-dihydro-2-ethyl-1H-inden-2-yl) imidazole.

Another synthetic route for obtaining 5-(2-ethyl-2,3-dihydro-1H-inden-2-yl)-1H-imidazole is disclosed in WAI, Wonf, et al. A Concise Synthesis of Atipamezole. *Synthesis*. 1995, no. 2, p. 139-140. The cyclization of alpha, alpha'-dibromo-o-xylene with acetylacetone by means of NaOH and tetrabutylammonium bromide in toluene/water at 80° C. under phase-transfer conditions gives the unstable diacetyl derivative, which presumably undergoes cleavage to afford 2-acetylindane. The alkylation of 2-acetylindane with ethyl iodide and potassium tert-butoxide yields 2-acetyl-2-ethylindan, which is brominated with $Br_2$ to give 2-bromoacetyl-2-ethylindan. Finally, this compound is cyclised with formamide at 160° C. (some 2-ethyl-2-(4-oxazolyl)indane is also formed but easily eliminated); the cyclization can also be carried out with formamidine in liquid ammonia.

Although the substitution of formamide by formamidine acetate eliminates the oxazole formation, it does not increase the yield of Atipamezole (<30%) WAI, Wonf, et al. A Concise Synthesis of Atipamezole. *Synthesis*. 1995, no. 2, p. 139-140 in the final step.

DISCLOSURE OF INVENTION

The bromination of ketone by using bromine in dichloromethane was sluggish and led to many byproducts;

Converting bromo ketone to Atipamezole using formamide at 160° C., Atipamezole was formed as the minor product. The major product in this reaction was the oxazole. The EP 0310745 B (FARMOS OY) Apr. 12, 1989 which describes this reaction did not mention the formation of any oxazole, and the yield of the reaction was not disclosed.

The instant invention provides processes useful in the preparation of Atipamezole. The invention further provides intermediates useful in the preparation of Atipamezole, and processes useful in the production of such intermediates. Moreover it will be evident for the person skilled in the art that this novel method provides convenient route to new analogues of Atipamezole not attainable by the known methods, as well as to new derivatives of indane-1,3-dione.

The above objective is achieved according to the present invention by sequential combination of four process steps, starting from 1-trityl-1H-imidazole-4-carboxaldehyde:

(a) condensation of phtalide to 1-trityl-1H-imidazole-4-carboxaldehyde (I), and, thus preparation of 2-(1-trityl-1H-imidazole-4-yl)indan-1,3-dione (II);

(b) alkylating of 2-(1-trityl-1H-imidazole-4-yl)indan-1,3-dione with ethyl iodide to produce 2-ethyl-2-(1-trityl-1H-imidazole-4-yl)indan-1,3-dione (III);

(c) removing the trityl group of 2-ethyl-2-(1-trityl-1H-imidazole-4-yl)indan-1,3-dione by acid hydrolysis to yield the deprotected 2-ethyl-2-(1H-imidazol-2-yl) indan-1,3-dione (IV);

(d) reducing the product of step (c) by catalytic hydrogenation to form the desired 5-(2-ethyl-2,3-dihydro-1H-inden-2-yl)-1H-imidazole hydrochloride (V).

In another aspect of the present invention, there is provided new valuable intermediates for preparing Atipamezole and analogues thereof, as well as new derivatives of indane-1,3-dione, namely 2-(1-trityl-1H-imidazole-4-yl)indan-1,3-dione (II) and 2-ethyl-2-(1-trityl-1H-imidazole-4-yl)indan-1,3-dione (III).

Reaction Scheme 1

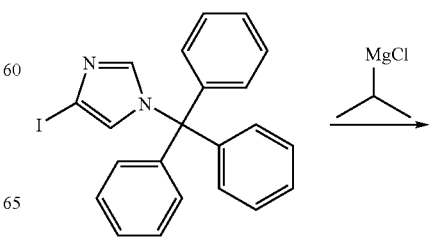

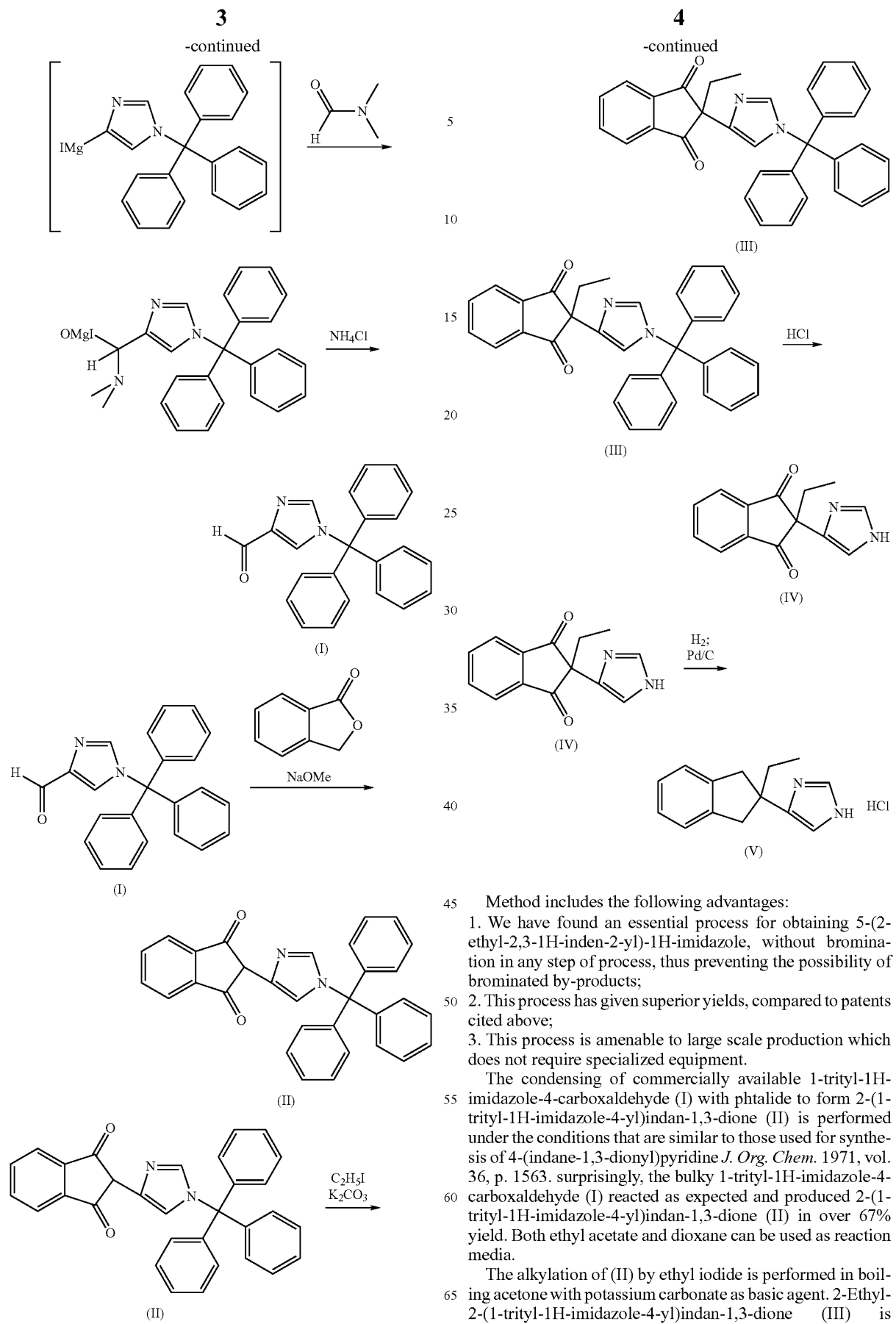

Method includes the following advantages:
1. We have found an essential process for obtaining 5-(2-ethyl-2,3-1H-inden-2-yl)-1H-imidazole, without bromination in any step of process, thus preventing the possibility of brominated by-products;
2. This process has given superior yields, compared to patents cited above;
3. This process is amenable to large scale production which does not require specialized equipment.

The condensing of commercially available 1-trityl-1H-imidazole-4-carboxaldehyde (I) with phtalide to form 2-(1-trityl-1H-imidazole-4-yl)indan-1,3-dione (II) is performed under the conditions that are similar to those used for synthesis of 4-(indane-1,3-dionyl)pyridine *J. Org. Chem.* 1971, vol. 36, p. 1563. surprisingly, the bulky 1-trityl-1H-imidazole-4-carboxaldehyde (I) reacted as expected and produced 2-(1-trityl-1H-imidazole-4-yl)indan-1,3-dione (II) in over 67% yield. Both ethyl acetate and dioxane can be used as reaction media.

The alkylation of (II) by ethyl iodide is performed in boiling acetone with potassium carbonate as basic agent. 2-Ethyl-2-(1-trityl-1H-imidazole-4-yl)indan-1,3-dione (III) is formed in over 67% yield and easily isolated from the acetone solution by concentrating it and diluting with water. A high purity (III) is obtained after crystallization from methanol or ethanol.

Removing the trityl group of 2-ethyl-2-(1-trityl-1H-imidazole-4-yl)indan-1,3-dione by acid hydrolysis to yield the deprotected 2-ethyl-2-(1H-imidazol-2-yl)indan-1,3-dione.

The reduction of (IV) to 5-(2-ethyl-2,3-dihydro-1H-inden-2-yl)-1H-imidazole hydrochloride (V) is performed in hydrogenation apparatus with Pd/C catalyst under hydrogen pressure in HCl solution. The reaction proceeds under variable pressure and temperature conditions, but a pressure of about 3 bar and the temperature of about 80-85° C. is preferable. After removing the catalyst the product crystallizes on chilling in over 77% yield. It can be purified by additional crystallization.

The present invention will be described in more detail by referring to the following non-limiting examples.

EXAMPLE 1

Preparation of
1-trityl-1H-imidazole-4-carboxaldehyde

1-Trityl-4-iodoimidazole (87.3 g, 0.200 mol) was added to stirred methylene chloride (525 mL) in a 4-neck round bottom flask fitted with a mechanical stirrer, a thermometer, a dropping funnel and a tube for argon introduction into the reaction mixture.

The reaction mixture was cooled to 10° C., at which point isopropylmagnesium chloride solution in tetrahydrofuran (112 mL, 0.213 mol) was added dropwise under an argon atmosphere. After addition of isopropylmagnesium chloride the reaction mixture was warmed to 20° C.

N,N-Dimethylformamide (47 mL, 0.608 mol) was added to methylene chloride (300 mL) in a 4-neck round bottom flask fitted with a mechanical stirrer, a thermometer, a dropping funnel and a tube for argon introduction into the reaction mixture. The reaction mixture was stirred and cooled to (−5)° C. and solution of the imidazole Grignard derivative, which was prepared above, was added to the reaction mixture. The reaction mixture was stirred at (−5)° C. for half an hour and then at 20° C. for 10 hours, at which point 10% aqueous ammonium chloride solution (300 mL) was added to the reaction mixture.

The aqueous layer was extracted with methylene chloride (550 mL). The organic layer was separated and washed with saturated sodium chloride solution, and then the organic layer was stirred with anhydrous magnesium sulphate for 2 hours. The precipitate of magnesium sulphate was separated by filtration.

The solvent was removed by distillation at a reduced pressure. Ethanol (200 mL) was added to the distillation residue and the reaction mixture was cooled to (−5)° C. for 2 hours.

The precipitates were separated by filtration. The obtained intermediate 1-trityl-1H-imidazole-4-carboxaldehyde was dried at under reduced pressure. The yield was 56.6 g (73.2%).

EXAMPLE 2

Preparation of
2-(1-trityl-1H-imidazole-4-yl)indan-1,3-dione

1-Trityl-1H-imidazole-4-carboxaldehyde (120 g, 0.319 mol) and phthalide (42.8 g, 0.319 mol) were added to stirred ethyl acetate (1000 mL) in a 4-neck round bottom flask fitted with a mechanical stirrer, a thermometer, a dropping funnel and a reflux condenser.

Meanwhile sodium methoxide (51.7 g, 0.957 mol) was added to cooled methanol (500 mL) in a separate vessel.

Thereafter the methanolic solution of sodium methoxide was added to the reaction mixture at 60° C. and was heated at this temperature for 3 hours and then cooled to 30° C., at which point the solvent was removed by distillation at a reduced pressure.

The distillation residue was poured into water and aqueous hydrochloric acid solution was added, until pH=4-5. The solid orange-brownish precipitates were filtered, the crude product of 2-(1-trityl-1H-imidazole-4-yl)indan-1,3-dione was washed on filter with water.

After the recrystallization of crude 2-(1-trityl-1H-imidazole-4-yl)indan-1,3-dione from ethanol the yield of the 2-(1-trityl-1H-imidazole-4-yl)indan-1,3-dione intermediate product was 97.4 g (67.2%), having a melting temperature of 213 to 215° C.

EXAMPLE 3

Preparation of 2-ethyl-2-(1-trityl-1H-imidazole-4-yl)
indan-1,3-dione

The intermediate 2-(1-Trityl-1H-imidazole-4-yl)indan-1,3-dione (79.4 g, 0.175 mol), potassium carbonate (72.5 g, 0.875 mol) and ethyl iodide (71 mL, 0.522 mol) were added to stirred acetone (1300 mL) in a 4-liter glass reactor, fitted with a mechanical stirrer, a thermometer and a reflux condenser. The reaction mixture was heated to reflux for 7 hours, then cooled to 20° C. and filtered. The inorganic residue on the filter was washed with acetone. The filtrate was concentrated in vacuo and poured into water.

The mixture was stirred at 20° C., the solid yellow-reddish precipitate was filtered, and the crude 2-ethyl-2-(1-trityl-1H-imidazole-4-yl)indan-1,3-dione was washed on the filter with water.

After the recrystallization of crude of 2-ethyl-2-(1-trityl-1H-imidazole-4-yl)indan-1,3-dione from ethanol, the yield of 2-ethyl-2-(1-trityl-1H-imidazole-4-yl)indan-1,3-dione was 43.6 g (50.9%), having a melting temperature of 196-197° C.

EXAMPLE 4

Preparation of
2-ethyl-2-(1H-imidazol-1-yl)indan-1,3-dione

2-Ethyl-2-(1-trityl-1H-imidazole-4-yl)indan-1,3-dione (93.4 g, 0.193 mol) was added to stirred 2N hydrochloric acid (650 mL) in a 3-neck round bottom flask fitted with a mechanical stirrer, a thermometer and a reflux condenser. The reaction mixture was heated at 100° C. for 3 hours.

Thereafter the reaction mixture was cooled to 25° C., at which point the reaction mixture was filtered to remove triphenylmethanol. The filtrate was cooled and 20% sodium hydroxide (276 mL) was added.

The precipitate was separated by filtration and washed with water (700 mL). The obtained intermediate 2-ethyl-2-(1H-imidazol-4-yl)indan-1,3-dione was dried under reduced pressure. The yield was 35.7 g (76.2%) of white crystalline 2-ethyl-2-(1H-imidazol-4-yl)indan-1,3-dione.

EXAMPLE 5

Preparation of crude 5-(2-ethyl-2,3-dihydro-1H-inden-2-yl)-1-H-imidazole hydrochloride 2-Ethyl-2-(1-trityl-1H-imidazole-4-yl)indan-1,3-dione (26.8 g, 0.056 mol) was added to stirred 5N hydrochloric acid (200 mL) in a 3-neck round bottom flask fitted with a mechanical stirrer, a thermometer and a reflux condenser. The reaction mixture was heated at 100° C. for 3 hours.

Thereafter the reaction mixture was cooled to 25° C., at which point the reaction mixture was filtered to remove triphenylmethanol. The triphenylmethanol cake on the filter was washed with 5N hydrochloric acid (100 mL). The filtrate was mixed with activated charcoal and stirred for 10 minutes; the charcoal was separated by filtration.

A hydrochloric acid solution of 2-ethyl-2-(1H-imidazol-4-yl)indan-1,3-dione hydrochloride was obtained.

Palladium catalyst (1.4 g of 10% Pd/C) was suspended in the hydrochloric acid solution of 2-ethyl-2-(1H-imidazol-4-yl)indan-1,3-dione hydrochloride. The obtained suspension was poured into a hydrogenation autoclave. Hydrogen was supplied to autoclave to 3.0 bar. The reaction mixture was stirred and heated to 80-85° C. The typical hydrogenation time was 6 hours. After hydrogenation the reaction mixture was filtered to remove the catalyst. The filtrate was cooled to (−5)° C., the precipitates were separated by filtration. The obtained crude 5-(2-ethyl-2,3-dihydro-1H-inden-2-yl)-1H-imidazole hydrochloride was dried at 50° C. under reduced pressure. The yield was 3.7 g of a white powder.

Alternatively, the filtrate of reaction mixture was concentrated in vacuo almost to dryness. Acetone (50 mL) was added to the stirred reaction mixture and thereafter the solvent was removed by distillation at a reduced pressure. Another portion of acetone (40 mL) was added to the reaction mixture. The reaction mixture was cooled to 0° C. for 4 hours.

The suspension was filtered; the crude product was washed with acetone on the filter.

EXAMPLE 6

Preparation of 5-(2-ethyl-2,3-dihydro-1H-inden-2-yl)-1H-imidazole hydrochloride

The crude 5-(2-ethyl-2,3-dihydro-1H-inden-2-yl)-1H-imidazole hydrochloride (12.5 g) was added to stirred acetonitrile (162 mL) and water (14 mL) in a 3-neck round bottom flask fitted with a mechanical stirrer, a thermometer and a reflux condenser.

The reaction mixture was stirred at 75-80° C. the reaction mixture was filtered, and the filtrate was cooled to 0-5° C.

The precipitates were separated by filtration and the product cake on the filter was washed with acetone (50 mL). The 5-(2-ethyl-2,3-dihydro-1H-inden-2-yl)-1H-imidazole hydrochloride was dried at 80-90° C. under reduced pressure. The yield was 9.8 g (77.3%) of colourless crystalline powder.

The invention claimed is:

1. A process for preparing 5-(2-ethyl-2,3-dihydro-1H-inden-2-yl)-1H imidazole hydrochloride of formula (V)

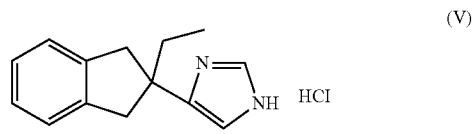

(V)

comprising the steps of:
a) condensing 1-trityl-1H-imidazole-4-carboxaldehyde with phtalide to form 2-(1-trityl-1H-imidazole-4-yl)indan-1,3-dione,
b) alkylating the product of step (a) with ethyl iodide to form 2-ethyl-2-(1-trityl-1H-imidazole-4-yl)indan-1,3-dione,
c) removing the trityl group from the product of step (b) by acid hydrolysis to form 2-ethyl-2-(1H-imidazol-4-yl)indan-1,3-dione,
d) reducing the product of step (c) by catalytic hydrogenation to form the desired 5-(2-ethyl-2,3-dihydro-1H-inden-2-yl)-1H imidazole hydrochloride.

2. The process according to claim 1, wherein step a) is carried out in an organic solvent comprising ethyl acetate in the presence of a methanolic solution of sodium methoxide.

3. The process according to claim 1, step b) is carried out by alkylation of a compound of formula (II) by ethyl iodide and alkali metal carbonate.

4. The process according to claim 3, wherein the alkali metal carbonate is potassium carbonate.

5. The process according to claim 1, wherein step c) is carried out using hydrochloric acid.

6. The process according to claim 1, wherein step d) is carried out by catalytic hydrogenation using hydrochloric acid solution in the presence of Pd/C catalyst.

7. A compound which is 2-(1-Trityl-1H-imidazole-4-yl)indan-1,3-dione.

8. A compound which is 2-Ethyl-2-(1-trityl-1H-imidazole-4-yl)indan-1,3-dione.

* * * * *